United States Patent [19]

Rosenberg

[11] Patent Number: 5,532,231

[45] Date of Patent: Jul. 2, 1996

[54] ANTIBACTERIAL AGENT

[75] Inventor: Eugene Rosenberg, Givat-Shmuel, Israel

[73] Assignee: Ramot University Authority for Applied Research and Industrial Development Ltd., Tel-Aviv, Israel

[21] Appl. No.: 332,964

[22] Filed: Nov. 1, 1994

[51] Int. Cl.[6] .................... A61K 31/395; C07D 267/00
[52] U.S. Cl. ................................ 514/183; 540/454
[58] Field of Search ................ 540/454; 514/183

[56] References Cited

U.S. PATENT DOCUMENTS 3,973,005   8/1976   Rosenberg ..................... 424/115

OTHER PUBLICATIONS

Trowitzsch et al I, "Structure of Myxovirescin A, etc" J. Chem. Soc. Commun. (1982), (23), 1340–2.

Trowitzsch et al II, "Antibiotics from Gliding, etc" Liebigs Ann. Chem. 1985, 1629–1652.

*Primary Examiner*—Patricia L. Morris
*Attorney, Agent, or Firm*—William C. Gerstenzang; Sprung Horn Kramer & Woods

[57] ABSTRACT

A compound having the following formula:

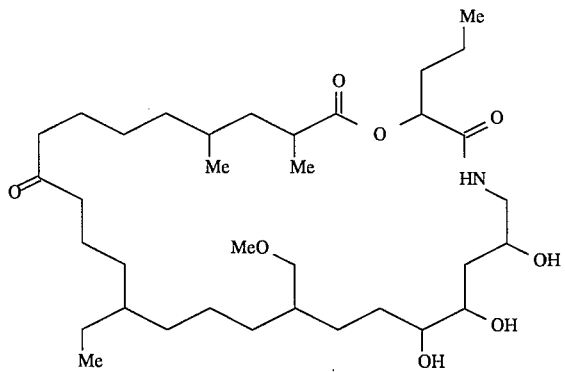

wherein Me represents a methyl group, having an antibacterial activity.

2 Claims, 7 Drawing Sheets

ANTIBACTERIAL AGENT

FIELD OF THE INVENTION

The present invention concerns an antibiotic drug. The present invention also concerns pharmaceutical preparations comprising the drug as well as method of treatments making use of same.

BACKGROUND OF THE INVENTION AND PRIOR ART

In the following, reference will be at times made to prior art documents, the full particulars of which is to be found at the end of the description before the claims.

Myxobacteria are Gram-negative, rod-shaped bacteria commonly found in soil and decay vegetation (Kaiser et al., 1979). Myxobacteria are generally a rich source of antibacterial agents, that exhibit a wide range of chemical structures, mode of action and anti-microbial spectrum (Rosenberg and Varon, 1984). One strain, *M. xanthus* TA, produces a broad spectrum antibacterial agent when grown under nutritionally limited conditions, during the end of its exponential growth phase. This antibacterial agent which is disclosed in Rosenberg, U.S. Pat. No. 3,973,005 was termed "TA", and is capable of inhibiting growth of a variety of Gram-positive and Gram-negative bacteria (Dworkin & Kaiser, 1985; Rosenberg et al., 1973). The growth inhibition is caused by lysis of growing bacteria as a result of blocking of cell wall synthesis at the stage of polymerization of the lipid disaccharide-pentepeptide (Rosenberg et al., 1973; Zafriri et al., 1981).

Figure 1:
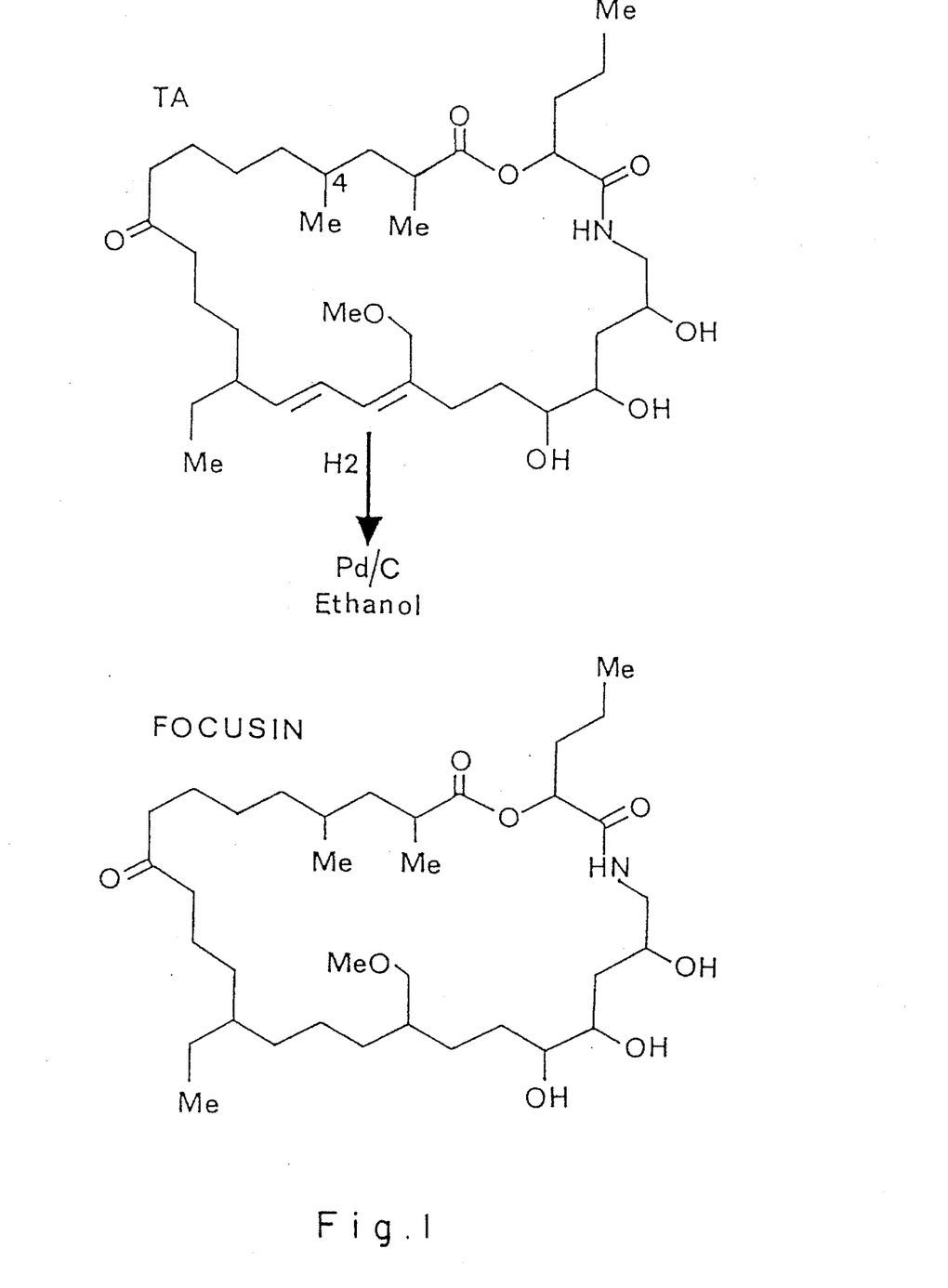
FIG. 1 is a schematic representation of the hydrogenation reaction of TA to produce Focusin.

TA is a molecule with a molecular weight of 623.8 dalton, and having the molecular formula $C_{34}H_{57}O_9N$ (Rosenberg et al., 1982; see FIG. 1 for its structure). TA binds tightly to a variety of tissues and surfaces and retains its activity while in the bound form (Manor et al., 1985; Rosenberg et al., 1984). For example, TA binds to dental hard and soft tissues, which allowed the use of this antibiotic to treat severe gingivitis and to reduce plaque in humans (Manor et al., 1989). One of the disadvantages of the TA antibiotic is that it loses its activity following simultaneous exposure to air and light (Rosenberg et al., 1982). An antibiotic drug showing some of the beneficial properties of TA antibiotics but being stable to such exposure, will be highly desirable. The present invention aims at the provision of such an antibiotic drug.

SUMMARY OF THE INVENTION

In accordance with the invention a novel compound, termed herein as "Focusin", has been prepared and found to have a broad spectrum antibacterial activity against both Gram-positive and Gram-negative bacteria. Focusin was found to have a similar activity spectrum to that of TA although with a somewhat lower specific activity. However, Focusin was found to be much more stable to exposure to light and air than the TA antibiotic. Focusin further has a higher aqueous solubility than TA and it also adheres more strongly than TA to a variety of surfaces and is released therefrom more slowly than TA. Like TA, Focusin adhered to soft and hard tissues, and it retains its bactericidal activity in the bound form. These properties of focusin allow its use for a wide range of applications where the TA antibiotic would be unsuitable.

In accordance with one aspect of the invention there is provided a compound, termed herein as "Focusin", having the following formula I:

wherein Me represents a methyl group.

In accordance with another aspect of the invention there is provided a pharmaceutical preparation comprising an effective amount of the compound of formula I and a pharmaceutically acceptable carrier or diluent.

The term "effective amount" should be understood as meaning an amount of Focusin sufficient to bring about a bactericidal activity.

A particular and preferred application of Focusin is in uses requiring adherence of an antibacterial drug to solid surfaces, to be slowly released therefrom over a period of time. One example of such use is in dental medicine, e.g. in the treatment of gingivitis or plaque where Focusin may be applied so that it adheres to the teeth or gingiva and is then slowly released therefrom thus exerting its activity over a period of time. Another example of use of Focusin in dental medicine is in a form in which it is adhered to a carrier intended to be placed at a needed site in the mouth.

Focusin may also be used in medical devices having parts intended for insertion into body cavities. Such parts come into contact with surrounding tissue and often, where the contact is for prolonged periods of time, bacterial infections may arise. In such uses, Focusin may be adhered to surfaces which come into contact with the surrounding tissue and this antibacterial agent which will be released for a period of time, will thus inhibit bacterial infections. One example of such use is in urological catheters (catheters intended to be inserted into the urethra for draining of urine from the bladder). It should be noted that infections of urinary tracts are a common complication of urinary tract catheterization. In accordance with the invention, Focusin will be adhered to the catheter's external surface whereby growth of bacteria at the contact area of the catheter with the surrounding tissue will be inhibited.

The present invention also provides a process for producing Focusin comprising hydrogenating the TA antibiotic.

The present invention will now be illustrated in the following description of examples carried out within the framework of the present invention. As will be appreciated, the invention is not limited to the specifically disclosed embodiments.

BRIEF DESCRIPTION OF THE DRAWINGS

In the drawings:

FIG. 6 shows the effect of the antibacterial agents' concentration on the ratio of antibiotic bound to polystyrene versus that which was released ("bound/released")

DESCRIPTION OF SPECIFIC EMBODIMENTS

The experiments performed within the framework of the present invention will now be described below:

MATERIALS AND METHODS

1. Bacterial strains

The following bacterial strains were used in the experiments below:

*Escherichia coli* ESS Kan$^r$, is a kanamycin resistant strain of *E. coli* ESS, derived by transducing *E. coli* ESS with P1:TnV, Kan$^r$. This strain was used for the standard antibiotic assays.

Other strains which were used were the following:

*Salmonella thyphimorium, Erwinia herbicolla, Serratia marcescens, Providencia strautii* and *Proteus vulgaris,* Enterobacter, Klebsiella Gr47, *Klebsiella pneumoniae,* Klebsiella sp., *Citrobacter diversus, Staphylococcus aureus, Pseudomonas aeruginosa, Escherichia Coli* K-12, *Bacillus subtilis* and *Staphylococcus albus* and *Mycobacterium smegmatis, Helicobacter pilori.*

2. Media and growth conditions

*E. coli* ESS Kan$^r$ was maintained by periodic transfer of single colonies for overnight incubation on LB Kan agar at 37° C., followed by further storage at 10° C. for 4–6 weeks. LB Kan medium is 1% Tryptone (Difco Laboratories, Detroit Mich. U.S.A.) containing 0.5% Yeast Extraction Extract (Difco), 0.5% NaCl (Merck & Co. Inc. Rahway, N.J. U.S.A.) and 50 µg/ml Kanamycin monosulfate (Sigma Chemical Company, St. Louis, U.S.A.).

LB Kan medium was solidified by 1.5% Bacto agar (Difco). For the antibiotic assay, Nutrient Broth agar plates were used. NB medium is 0.8% Nutrient Broth (Difco) containing 0.5% NaCl (Merck). NB was solidified by 1.8% Bacto agar (Difco). The NB plates were overlaid by 3.5 ml NB soft agar (0.9% Bacto agar) mixed with 0.1 ml *E. coli* ESS Kan$^r$ overnight culture.

3. Paper disc filter antibiotic assay

Antibiotic activity against *E. coli* ESS Kan$^r$ was determined by the paper disc filter assay (Leo et al., 1945). Unknown quantities of antibiotic TA or Focusin, dissolved in ethanol, saline or NB were applied to paper disc filters (6 mm diameter; Schleicher and Schull). After allowing the ethanol to evaporate in the hood for about 15 mins, the dry filters were placed on nutrient broth plates which had been overlaid with an overnight culture of *E. coli* ESS Kan$^r$ as described above.

The diameter of the zone of inhibition was recorded after 18 hours in incubation at 37° C. The concentration of the antibacterial agents were determined from a standard inhibition curve prepared with known quantities of TA and Focusin.

4. Testing for antimicrobial spectrum of TA and Focusin

Saturated solutions of TA and Focusin were prepared by adding 1.14 µg TA and 7 µg Focusin to 1 ml LB (final conc. of 1% ethanol). About $10^5$ bacteria of various strains were then added. The control was bacteria in the same medium with no antibacterial agents. The bacteria were introduced at 37° C. with shaking at 100 rpm. When the control became turbid, viable cell count was performed on LB agar plates. Growth inhibition is presented as percentage of the no antibiotic control.

5. Preparation of Focusin

Focusin was prepared by hydrogenation of TA, in a manner shown schematically in FIG. 1. The procedure which was used for preparation was briefly as follows:

90 mg of TA were dissolved in 55 ml of ethanol to which there was added 60 mg of a catalyst consisting of charcoal containing 5% palladium. This suspension, contained in a glass bottle having a total volume of about 250 ml, was placed in a Parr Hydrogenation apparatus. The air in the bottle was removed by applying a vacuum until the liquid started to bubble. Hydrogen at a pressure of at least 15 PSI was then added and the bottle was shaken for about 2.5 hours. After completion of this hydrogenation step, the residual hydrogen was removed by the application of a vacuum. Then, solids were removed from the solution by filtering through a Whatman 1 mm filter. The material was then concentrated in a vacuum at a temperature of 30° C.–35° C., to a volume of about 10 ml.

Focusin was purified by preparative thin layer chromatography (TLC) using glass sheets pre-coated with a 2 mm layer of silica gel (Kieselgel $F_{254}$, Merck, Rahway, N.J., U.S.A.). After application of the hydrogenation product the TLC plate was dried and then developed with a solution of benzene:acetone (1:1, v/v). After drying, the relevant fractions were extracted from the silica gel by ethanol, and the antibacterial activity of each fraction was determined by the antibiotic disc bio assay.

6. Thin liquid chromatography (TLC)

Plastic sheets pre-coated with a layer of 0.2 mm silica-gel (k\Kieselgel $F_{5735}$, Merck) were used. After Focusin and TA were applied, the TLC plates developed with benzene:acetone (1:1, v/v). After drying of the chromatogram, it was stained with 5% $H_2SO_4$ in ethanol. The chromatogram was heated by placing it over a flame until the spots of TA and Focusin appeared.

7. Adherence to polystyrene

7.1 Adherence to polystyrene

The antibacterial agents (Focusin and TA) dissolved in ethanol were applied to small polystyrene petri dishes (3 cm diameter) and the ethanol was allowed to evaporate over a period of 15 minutes in a hood. For control, ethanol without the agents was applied to such dishes. To each petri dish, 1 ml of a nutrient broth was added. The petri dishes were then incubated at 37° C. at 50 rpm in a shaking device (New Brunswick Scientific, USA). Following each time interval, the NB was removed and a fresh NB was added.

At the end of the experiments, a solution of 100% ethanol was added to the petri dishes in order to extract the residual antibacterial agents that remained stuck to the polystyrene.

In order to check the antibacterial agents that were released from the polystyrene to the NB, 30 μl and 60 μl samples of the NB were applied to the paper disc filters and assayed as described under 3 above.

7.2 Adherence to polystyrene in the presence of E. coli ESS

In some experiments, the release of antibiotics was tested in the presence of *E. coli* ESS. In these experiments, the nutrient broth (NB) which was added to the petri dishes contain $10^5$ *E. coli* ESS (from a log culture). Each fresh NB which was added to the dishes contained the same amount of *E. coli* cells.

Prior to the performance of the disc assay, the *E. coli* cells were killed by the application of 20 μl of ethanol onto the disc, so as not to disrupt the bioassay.

8. Adherence to a biological tissue and activity of bound antibiotic

8.1 Adherence of TA and Focusin to mouse tissues

Two mice were sacrificed by exposure to ether. The bladder, eyes, intestines, lungs, heart, teeth, liver, spleen and kidneys were removed by dissection. Each experimental set consisted of three test tubes. A piece of each tissue type was placed in each of the three test tubes. The amount of tissue per tube were as follows: bladder ⅓, eye ½, intestine 1 cm, lung ½, heart ⅓, fang tooth ½, liver ⅓, spleen ⅓ and kidney ½. One test tube contained a control tissue which was treated only with the solvent used for dissolving the antibacterial agent, usually 50% ethanol. The second and third test tubes contained tissues were treated with 4 μg TA or 20 μg Focusin, respectively.

Following application of the antibacterial agent or the control solution, the tissues were allowed to dry in a hood for 30 mins., and then placed in the test tubes.

One milliliter of sterile saline was then added to each test tube and the tubes were then incubated with shaking (50 rpm) at 37° C. for one hour. The amount of antibacterial agent that was released to the saline was measured following chloroform extraction by the disc filter assay.

The tissues were then transferred to exponentially growing cultures of *E. coli* ESS in NB at a concentration of $10^5$ cells/ml. Incubation was at 37° C. and continued for 5 hours, following which the number of viable cells was checked.

8.2 Release of Focusin from mouse tissue

Focusin was tested in the same manner as that described above (under 8.1) with the exception that the tissues in the test tube were washed four times with a solution of 1 ml sterile saline. Each saline wash was for 1 hour at 37° C. Following incubation, the washing saline solution was added to an exponentially growing cultures of *E. coli* ESS in a concentration of $10^5$ cells/ml.

The cultures with the saline wash were incubated at 37° C. for 6 hours and then viable cell count was performed in order to estimate the amount of killing by the antibacterial agent that were released from the tissues. After the four washes the tissues were transferred to $10^5$ *E. coli* ESS log cultures and were then incubated for 5 hours. The tissues were transferred in this way for three times, each time the percentage of inhibition by the treated tissue was measured by viable count.

RESULTS

9. Preparation and chemical properties of Focusin

Focusin was prepared by hydrogenation of TA, as described under 5 above. As can be seen in FIG. 1, following the hydrogenation reaction, the two double bonds between carbons 14–15 and 16–17 present in TA were saturated.

In order to check the hydrogenation product, TLC was performed as described above under 6. The starting material, TA, absorbed in the UV range at 254 nm owing to the two double bonds. Following reaction and the hydrogenation of the two double bonds, no UV absorption was observed with Focusin.

The NMR of Focusin gave the same spectra as antibiotic TA except for the addition of four new protons corresponding to the hydrogenation of the two double bonds (results not shown), which verified the structure of Focusin as shown in FIG. 1.

10. TLC purification

Glass sheets precoated with silica-gel (2 mm), Kieselgel $F_{254}$ were used. 10 mg of Focusin was applied, and the TLC plates were developed with benzene:acetone (1:1, v/v). After drying of the chromatogram, 1 cm pieces were scratched to the width of the plate. The fractions were then extracted by ethanol for several times and the disc filters bioassay (3 above) was performed in order to find the active fraction. TLC on small plastic plates was performed in order to find out if the material was purified. After the relevant fraction was picked, the Focusin was dried and the dry weight of the purified antibacterial agent was 7.7 mg.

11. Solubility of Focusin and TA in ethanol and saline

Focusin and TA at concentrations of 3 mg/ml were diluted either in ethanol or in saline containing 1% ethanol to yield a final concentration in each case of 30 μg/ml. The solutions were mixed at 37° C. for one hour under shaking, and then were centrifuged at 5000 g for 10 minutes. Several samples were taken from the supernatants of the tubes and were applied on disc filters in order to determine the concentration of the antibacterial agents in the saline and ethanol solutions, by the paper disc bioassay method.

TA and Focusin, as measured according to a standard inhibition curve (such a curve shown in FIG. 2) were completely soluble in ethanol; however, the solubility in saline for Focusin was about 7 μg/ml, whereas for TA it was about 1.14 μg/ml.

12. Activity of Focusin against *E. coli* ESS

Figure 2:
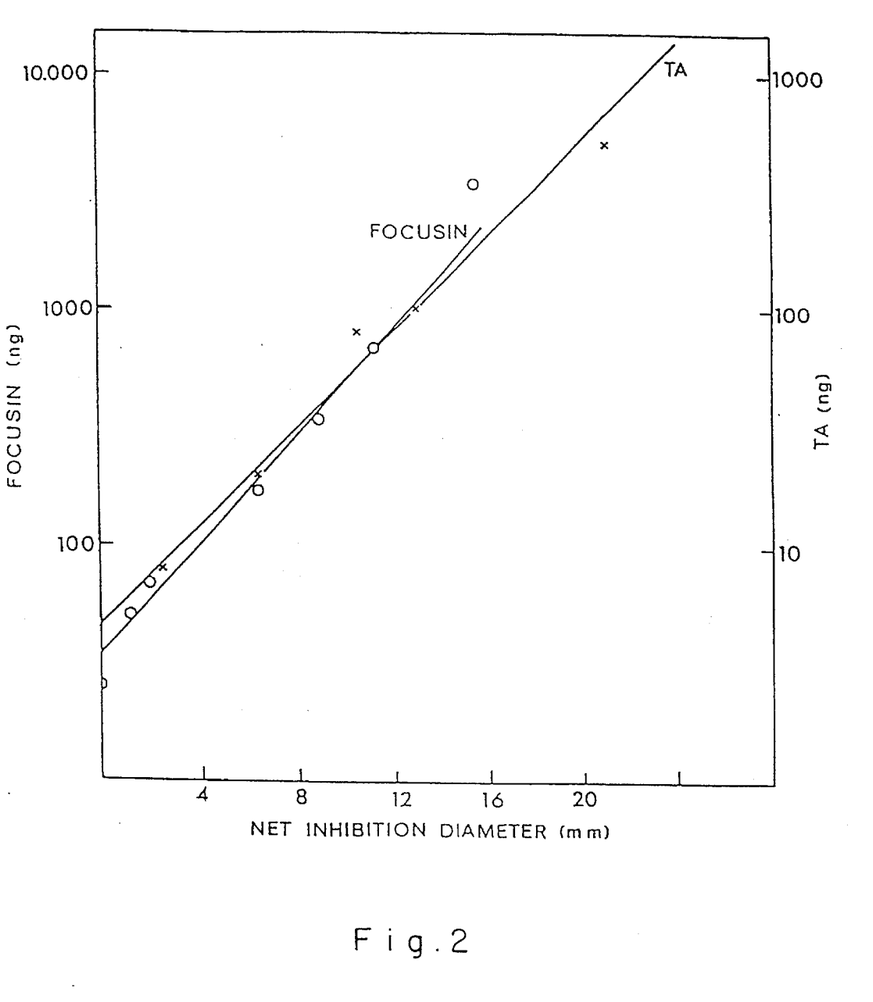
FIG. 2 shows inhibition curves of the antibacterial agents, TA (x) and Focusin (o) against *E. coli* ESS Kan$^r$ (a strain of FIG. 3 shows the activity of TA (o) and Focusin (●) against *E. coli* ESS as a function of the agents' concentration. This test was carried out in a liquid medium.

Standard inhibition curves of TA and Focusin against *E. coli* ESS are shown in FIG. 2. As can be seen, Focusin was quite active against *E. coli* ESS, showing a clear zone of inhibition with only 60 ng of this compound. However, Focusin had approximately ⅛ of the activity of TA at low concentrations: for example, in order to obtain a zone of inhibition of about 2 mm, 7.5 ng of TA were required as compared to 60 ng of Focusin. At high concentrations, Focusin had only a 1/10 of the TA activity: for example, inhibition zone of 11 mm was found with only 64 ng of TA compared to 640 ng of Focusin.

Figure 3:
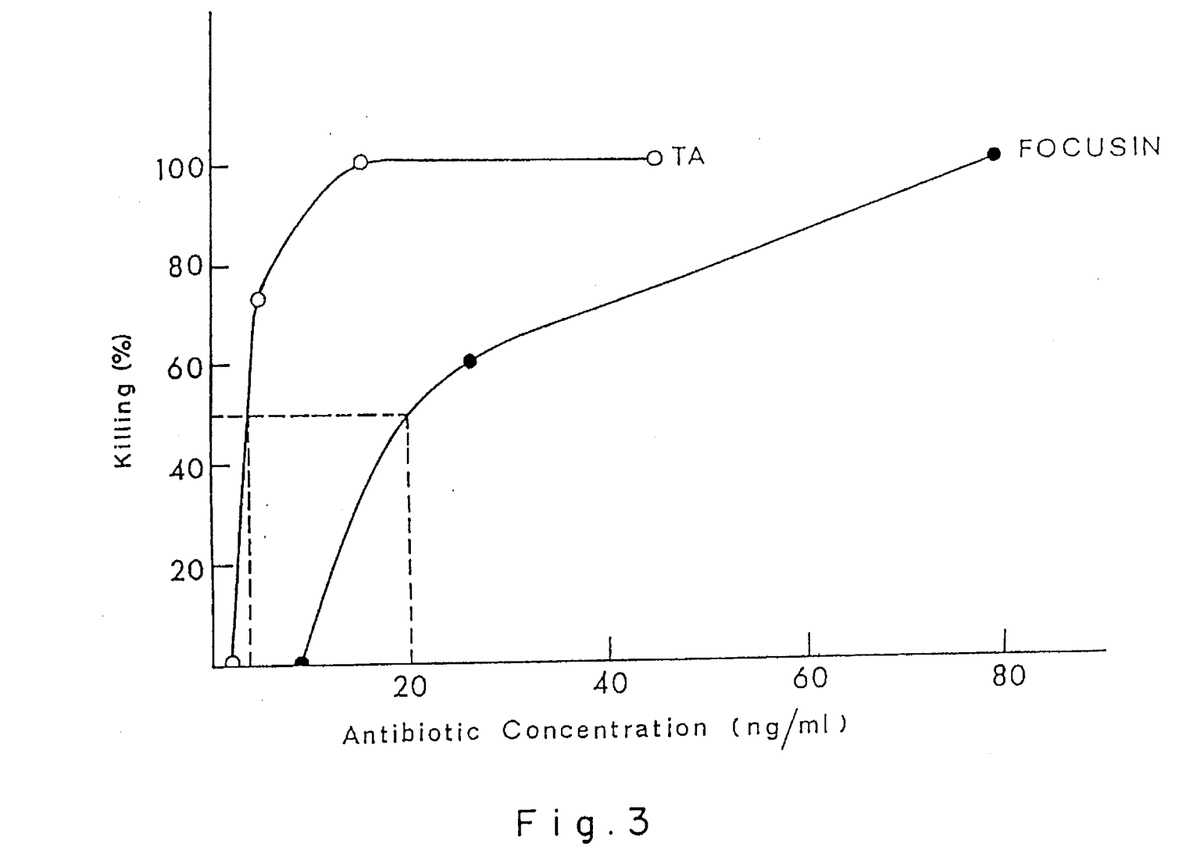

In a liquid medium the activity of Focusin could be noticed at a lower concentration. As can be seen in FIG. 3, the $LD_{50}$ values of TA and Focusin, were 4 ng/ml and 20 ng/ml, respectively. It is possible that part of the lower activity of Focusin, when applied to paper discs, was the greater binding of Focusin to the paper than TA.

13. Sensitivities to combined exposure to light and air of TA and Focusin 100 ng of TA and Focusin dissolved in ethanol were applied to paper filters and allowed to dry in a hood for 15 mins. The filters were then exposed to light from a fluorescent lamp in the hood; the distance from the lamp to the filters was approximately 40 cm. The controls were placed in the dark under a plastic box within the hood.

After exposure of the filters to the light for varying periods of time, the remaining activity of the agents was measured by the paper disc bioassay and the results are shown in the following Table 1:

TABLE 1

| Antibiotics TA and Focusin light sensitivities | | |
|---|---|---|
| Hours | TA activity (%) | Focusin activity (%) |
| 0 | 100 | 100 |
| 1 | 70 | 100 |
| 4 | 63 | 100 |
| 6 | 26 | 100 |
| 8 | 21 | 100 |
| 20 | 19 | 100 |

As can be seen from the above results, Focusin was completely resistant to breakdown at a combined exposure to light and air for at least 20 hours, whereas TA was degraded by 30% after one hour and by 81% after 20 hours.

14. Antimicrobial spectrum of TA and Focusin

The sensitivities of various bacterial strains to TA and Focusin were tested in liquid media. The results are shown in the following Table 2.

TABLE 2

| Sensitivity of different bacteria to saturating concentrations of TA and Focusin | | |
|---|---|---|
| Strain | TA killing (%) | Focusin killing (7%) |
| *E. coli* K-12 | 100 | 100 |
| *Erwinia herbicola* | 100 | 100 |
| *Staphylococcus aureas* | 100 | 100 |
| *E. coli* ESS | 100 | 100 |
| *Salmonella thyphimurium* | 60 | 40 |
| Enterobacter | 100 | 100 |
| *Bacillus subtilis* | 100 | 100 |
| *Citrobacter diversus* | 100 | 100 |
| Klebsiella Gr47+ | 100 | 100 |
| Klebsiella sp+ | 100 | 60 |
| *Klebsiella pneumoniae*+ | 100 | 96 |
| *Proteus vulgaris* | 100 | 90 |
| *Serratia marcescens* | 100 | 67 |
| *Staphylococcus albus* | 83 | 73* |
| *Pseudomonas aeruginosa* | 0 | 0 |
| *Providencia strautii* | 100 | 100 |
| *Mycobacteria smegmatis* | 0 | 0 |
| *Helicobacter pilori* | 100 | 100 |

*On the 46th hour
+Hospital strains

The above results show that overall TA and Focusin had a similar antibacterial activity spectrum in the tested bacterial strains. All the tested strains, except two, *Pseudomonas aeruginosa* and *Mycobacterium smegmatis*, were sensitive to both TA and Focusin. However, six of the strains (*Salmonella thyphimurium*, Klebsiella sp., *Klebsiella pneumoniae*, *Proteus vulgaris*, *Serratia marcescens* and *Staphylococcus albus*) were only partially killed by Focusin, and two strains (*Salmonella thyphimurium* and *Staphylococcus albus*) were only partially killed by TA. The strain *Staphylococcus albus* began to show sensitivity to the antibacterial agents only after 46 hours of incubation.

Figure 4:
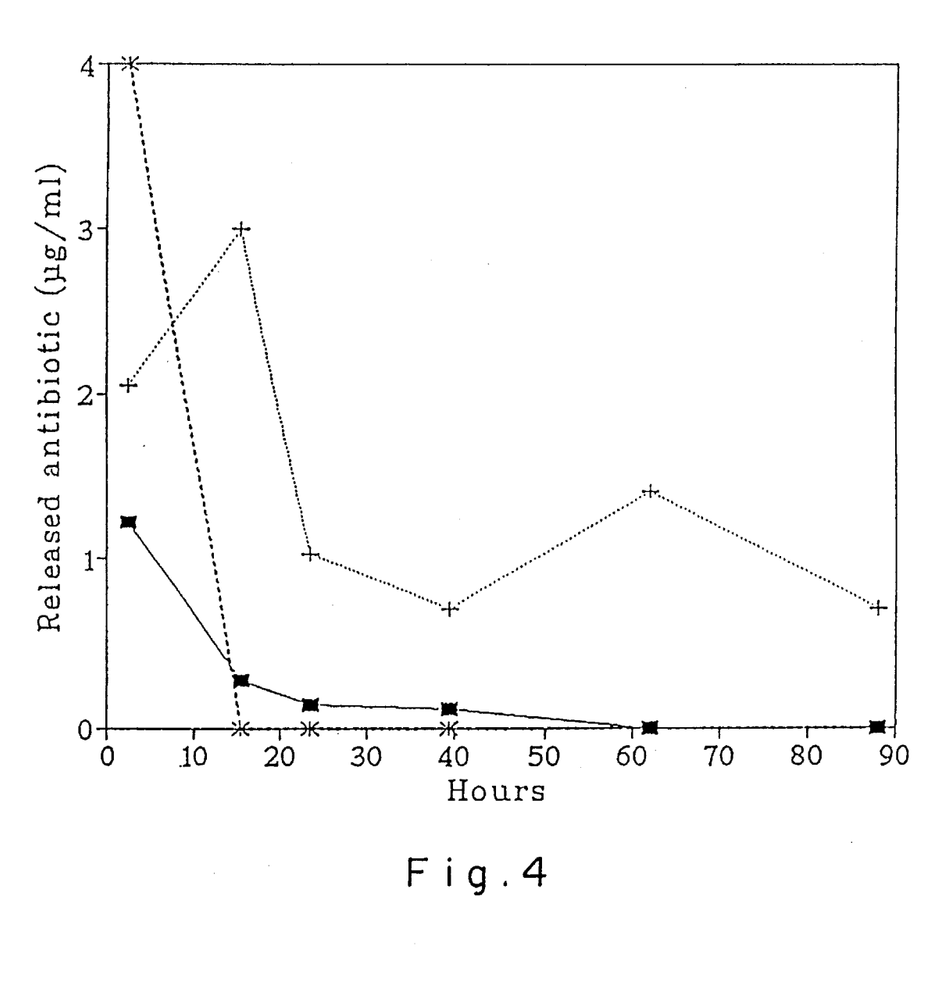
FIG. 4 shows the amount of TA (■), Focusin (+) and Ampicilin (*) absorbed to a polystyrene surface, release to a medium within several time intervals.

15. Adherence of TA, Ampiciilin and Focusin to polystyrene, in the presence of *E. coli* ESS 4 µg of TA, 20 µg of Focusin and 4 µg of Ampicillin, were each dissolved in 100% ethanol and were dried on polystyrene petri dishes, for 14 minutes in a hood. 1 ml of an exponentially grooving culture of *E. coli* ESS ($10^5$ cell/ml) in NB was then added to the plate. The plates were incubated at 37° C. under shaking at 50 rpm for various time intervals. Following each time interval, the NB was removed and fresh NB was applied with $10^5$ *E. coli* ESS. Release of antibacterial agents to the NB was measured by the paper disc filter assay and the results are shown in FIG. 4. As can be seen in FIG. 4, all the Ampicillin was released to the NB at the first wash while the release of TA and Focusin was much slower. TA was released continuously for four washes (40 hours), whereas Focusin, even after 88 hours, was still bound to the polystyrene and was slowly being released.

16. Adherence of TA and Focusin to polystyrene in the absence of *E. coli* ESS

This experiment was performed in a similar manner to that described under 15 with the exception that no *E. coli* ESS was added to the saline solution. Samples of 0.1 ml were withdrawn at varying time intervals and were assayed in the paper filter bioassay. At the end of the experiment the remaining antibacterial agent which was bound to the polystyrene was extracted by ethanol, and also measured by the paper filter bioassay.

Figure 5:
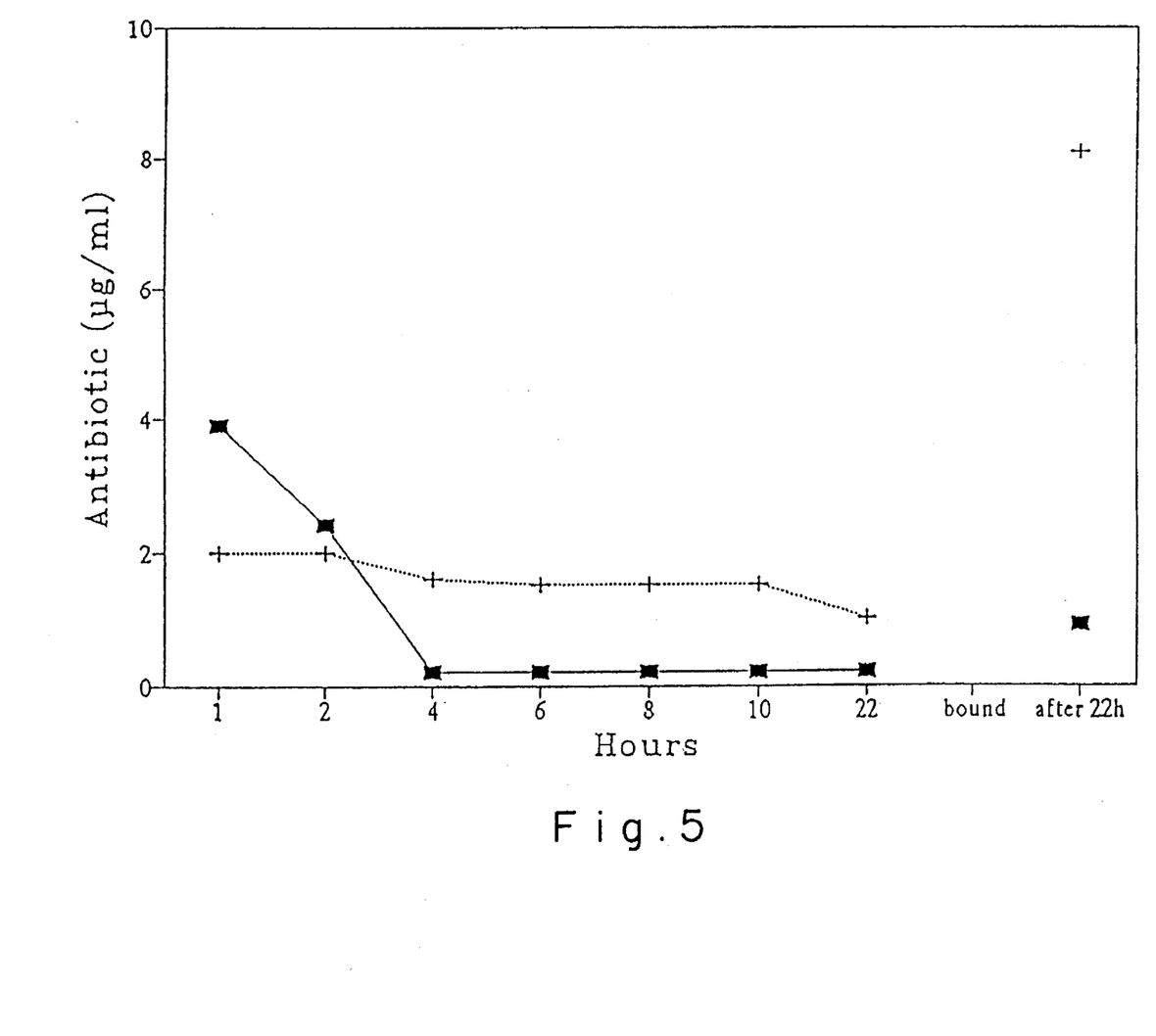
FIG. 5 shows the amount of TA (■) and Focusin (+) absorbed onto polystyrene surfaces, released to a medium within several time intervals, (similarly as in the experiment of FIG. 4). At the end of the experiment (after 22 hours) the amount of the antibacterial agent remaining absorbed to the polystyrene surface was determined by extraction with ethanol.

The results are shown in FIG. 5 and as can be seen, Focusin was released much slower than TA. At the beginning, TA was released quickly and following four hours, a small constant amount remained through the 22 hours of incubation. Against this, Focusin showed a slower initial and a much more prolonged release curve than TA. After 22 hours, 8 µg of Focusin and only 1 µg of TA were still bound to the polystyrene.

17. The effect of concentration on the adherence of TA and Focusin to polystyrene Several concentrations of TA (2 µg, 4 µg, 10 µg and 20 µg) and Focusin (10 µg, 20 µg, 50 µg and 100 µg), and 0.1 ml 100% ethanol (control) were dried on 3 sets of polystyrene petri dishes for 20 mins. in a hood. Sterile saline (1 ml) was added to each plate, after one hour incubation in 37° C. with shaking at 50 rpm, the amount of antibacterial agent released to the saline was checked by the paper disc assay. The remaining agent bound to the polystyrene, was dissolved by ethanol and measured in the same manner.

Figure 6A:
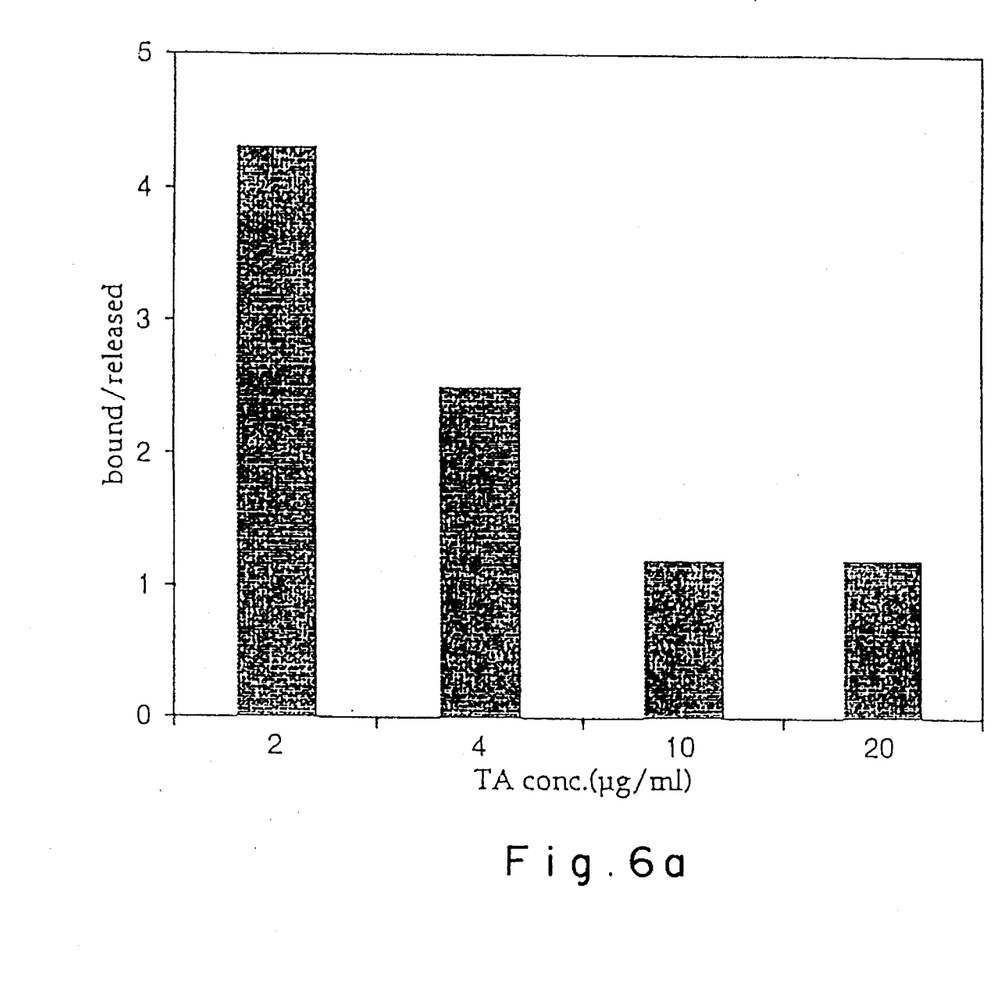
FIG. 6a—TA antibiotic.
Figure 6B:
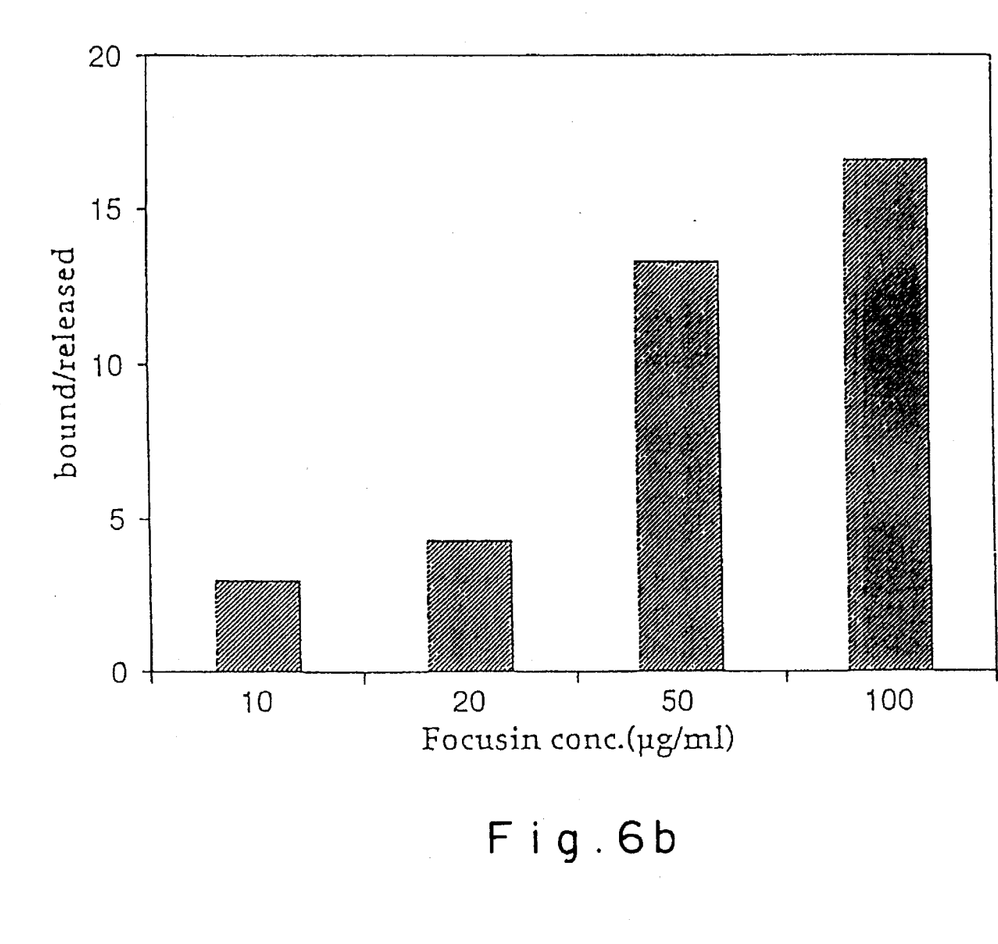
FIG. 6b—Focusin.

The results are shown in FIG. 6 depicting the effect of the antibacterial agent concentration on the bound/released ratio of the antibiotic to polystyrene. FIG. 6a shows that as the TA concentration increases, the amount of bound TA decreases; against this, as can be seen in FIG. 6b, the Focusin binding showed an increase bound/released ratio with an increase in concentration.

18. Adherence of TA and Focusin to mouse tissue and their bactericidal effect when bound to the tissue TA and Focusin were applied to mouse tissue, allowed to evaporate in a hood as described under 8.1. Following incubation, the amount of inhibition was assayed by viable cell counts (VCC) and the results are shown in the following Table 3:

TABLE 3

Adherence of TA and Focusin to mouse tissues and
their bactericidal effect when bound to the tissues

| Tissue | Released TA after 1 h saline wash (%) | Inhibition %* by the TA-tissue | Released Focusin after 1 h saline wash (%) | Inhibition %* by the Focusin-tissue |
|---|---|---|---|---|
| Liver | <3.7 | 96 | <2.9 | 94 |
| Lungs | 4.1 | 100 | 4.9 | 100 |
| Intestine | <3.7 | 99 | <3.1 | 100 |
| Heart | <3.0 | 100 | <3.2 | 90 |
| Teeth | 19.7 | 100 | <4.1 | 100 |
| Spleen | 6.0 | 100 | <4.1 | 100 |
| Kidney | 3.9 | 100 | <3.8 | 100 |
| Bladder | 15.8 | 100 | <4.1 | 100 |

*% Inhibition = $100 - \frac{\text{VCC experiment}}{\text{VCC control}} \times 100$ As can be seen in the above table, the teeth and bladder released relatively large quantities of TA's; however, the bound TA still caused 100% inhibition of E. coli. Against this, the liver and intestine lost only less than 3.7% of the initial amount of TA, and the remaining bound TA showed a 96% and 99% inhibition, respectively. Focusin was bound tightly to all tissues tested, more than 95% remained bound after the initial wash. After 5 hours with E. coli ESS more than 90% of the E. coli was inhibited (compared to control without antibacterial agent). The liver and heart tissues treated with Focusin did not completely inhibit the E. coli.

19. Release of Focusin from mouse tissue and the killing effect of the treated tissue Two sets of mouse tissue were treated, the first with 10 μg Focusin dissolved in 50% ethanol and the second only with ethanol, serving as a control (this solution did not contain an antibacterial agent). The tissues were treated as described in Section 8.2 above.

After the fourth wash, the treated tissues were transferred to E. coli ESS cultures ($10^5$ cells) in nutrient broth. The culture tubes were then incubated at 37° C. for 6 hours and the extent of growth inhibition was measured by viable cell count. The treated tissues were transferred to E. coli cultures two more times (a total of three times), and each time the percentage of growth inhibition by the treated tissues was checked. The results are shown in the following Table 4:

TABLE 4

Release of Focusin from mouse tissues and the
antimicrobial effect of antibiotic-bound tissues

| Tissue | Inhibition %* by the 4th wash liquid | Inhibition %* by the treated tissue** | Inhibition %* by the treated tissue*** |
|---|---|---|---|
| Liver | 67 | 99 | 100 |
| Lungs | 100 | 100 | 17 |
| Intestine | 100 | 100 | 38 |
| Heart | 100 | 100 | 98 |
| Teeth | 100 | 100 | 91 |
| Spleen | 100 | 100 | 98 |
| Kidney | 100 | 100 | 90 |
| Bladder | 100 | >99 | 0 |
| Eye | 100 | >99 | 0 |

*% Inhibition = $100 - \frac{\text{VCC experiment}}{\text{VCC control}} \times 100$

*After a single wash
**After two more transfers

The above results show that the bactericidal activity of the fourth liquid wash except for the liver tissue, contained enough Focusin to completely inhibit the E. coli growth. The washed tissues containing bound focusin showed a 99% inhibition or more. After the third transfer to the NB containing E. coli (a total of seven washes from the beginning), the liver was the only tissue that completely inhibited the E. coli. All the other tissues caused some inhibition, in decreasing order: heart and spleen (98%), teeth, kidney, intestine and lungs. However in bladder and eye insufficient Focusin was left and no inhibition was observed.

REFERENCES

1. Dworkin M. and Kaiser, D., 1985. Cell interactions in Myxobacterial growth and development, *Science*, 230:18–24.

2. Kaiser, D., Manoil C. and Dworkin, M., 1979. Myxobacteria:cell interactions, genetics and development, *Ann. Rev. Microbiol.*, 33:595–639.

3. Loo, Y. H., P. S. Skell, H. H. Thornberry, J. Ehrlich, J. M. McGuire, G. M. Savage and J. C. Silvester, 1945. Assay of streptomycin by the paper-disc plate method, *J. Bacteriol.*, 50:701–709.

4. Manor, A., Varon M., and Rosenberg E., 1985. Absorption of antibiotic TA to dental hard tissues, *J. Dental Res.*, 64:1371–1373.

5. Manor, A., Eli, I., Varon, M., Judes, H. and Rosenberg, E, 1989. Effect of adhesive antibiotic TA on plaque and gingivitis in man, *J. Clin. Periodontol.*, 16:281–284.

6. Rosenberg, E., 1976, U.S. Pat. No. 3,973,005.

7. Rosenberg, E., Vaks, B., and Zuckerberg, Z., 1973. Bactericidal action of an antibiotic produced by *Myxococcus xanthus, Antimicrob. Agents and Chemother.*, 4:507–513.

8. Rosenberg, E., Fytlovich S., Carmeli S. and Kashman, Y., 1982. Chemical properties of *Myxococcus xanthus* antibiotic, T. A. *J. Antibiotics*, 35:788–793.

9. Rosenberg, E., Porter, J. M., Nathan, P. D., Manor, A. and Varon, M., 1984. Antibiotic TA: an adherent antibiotic, *Biotechnology*, 2:796–799.

10. Rosenberg E., and Varon, M., 1984. Antibiotics and lytic enzymes. In: Myxobacteria: development and cell interactions. Rosenberg E. (Ed.) p. 109–125. Springer-Verlag, New York.

11. Zafriri, D., Rosenberg, E., and Mirelman, D., 1981. Mode of action of *Myxococcus xanthus* antibiotic TA. *Antimicrob. Agents and Chemother.*, 19:349–351.

I claim:

1. A compound having the formula I wherein Me represents a methyl group.

2. A pharmaceutical composition comprising a compound of the formula I wherein Me represents a methyl group, and a pharmaceutically acceptable carrier or diluent.

* * * * *